United States Patent [19]

Bottenbruch et al.

[11] Patent Number: 4,856,342
[45] Date of Patent: Aug. 15, 1989

[54] PROCESS AND DEVICE FOR MEASURING THE ADHESION OF FIBRES IN FIBRE-REINFORCED SYNTHETIC MATERIALS

[75] Inventors: Ludwig Bottenbruch; Hans-Joachim Traenckner, both of Krefeld; Andreas Hampe; Klaus Schumacher, both of Berlin, all of Fed. Rep. of Germany

[73] Assignee: Bayer Aktiengesellschaft, Leverkusen, Fed. Rep. of Germany

[21] Appl. No.: 170,492

[22] Filed: Mar. 21, 1988

[30] Foreign Application Priority Data

Apr. 9, 1987 [DE] Fed. Rep. of Germany ....... 3712073

[51] Int. Cl.⁴ .............................................. G01N 3/08
[52] U.S. Cl. ..................................................... 73/827
[58] Field of Search ................. 73/827, 831, 833, 834, 73/826, 801, 791, 792, 863, 150 A

[56] References Cited

U.S. PATENT DOCUMENTS

| | | | |
|---|---|---|---|
| 3,067,607 | 12/1962 | Crane et al. | 73/834 |
| 3,777,557 | 12/1973 | Dunlap | 73/791 |
| 4,041,806 | 8/1977 | Klar | 73/833 |
| 4,551,018 | 11/1985 | Mannava et al. | 73/657 |
| 4,572,001 | 2/1986 | Saimoto et al. | 73/826 |
| 4,662,228 | 5/1987 | Tse | 73/827 |
| 4,700,577 | 10/1987 | Tripp | 73/827 |

FOREIGN PATENT DOCUMENTS

| | | | |
|---|---|---|---|
| 1254355 | 8/1986 | U.S.S.R. | 73/827 |
| 1307312 | 4/1987 | U.S.S.R. | 73/150 A |
| 1199748 | 7/1970 | United Kingdom | 73/834 |

Primary Examiner—Stewart J. Levy
Assistant Examiner—Robert R. Raevis
Attorney, Agent, or Firm—Sprung Horn Kramer & Woods

[57] ABSTRACT

The adherence of an individual fibre embedded in a polymer matrix is determined by a drawing experiment in which the fibre is drawn out of the polymer matrix and simultaneously the pertaining force-distance diagram is registered. To this end a test sample consisting of the polymer matrix with the individual fibre embedded therein is manufactured by melting down a quantity of polymer present in granular or powder form on an object holder, the individual fibre is dipped into the molten polymer mass and the polymer mass is subsequently cooled down below the melting point. Subsequently the object holder with the test sample adhering thereto is brought into a force-distance measuring device, and the free end of the fibre is fixed to a chucking device moveable in the direction of the fibre. In the drawing experiment, the drawing force acting on the fibre is converted into corresponding electrical signals by the force transducer, and evaluated, and simultaneously the distance covered by the chucking device is converted into corresponding electrical signals by the distance transducer, and evaluated.

6 Claims, 2 Drawing Sheets

PROCESS AND DEVICE FOR MEASURING THE ADHESION OF FIBRES IN FIBRE-REINFORCED SYNTHETIC MATERIALS

BACKGROUND OF THE INVENTION

The invention relates to a process and a device for determining the adhesion of an individual fibre embedded in a synthetic material matrix. The process and the device are based on the carrying out of a drawing experiment, in which the fibre is drawn out of the synthetic material matrix and the associated force-distance diagram is simultaneously registered.

The mechanical characteristics, such as e.g. strength, the modulus of elasticity, or the dampening behaviour of fibre-reinforced synthetic material are paradigmatically determined by the adhesion strengths of the fibres in the synthetic material matrix. The adhesion force of the fibres can be measured directly by the drawing experiment referred to above. It is important therein that this measurement is of a single fibre. Otherwise, only undefined average values of relatively low informational content would be obtained.

One might think of preparing test samples of fibre-reinforced synthetic materials in such a manner that individual fibres project out of the synthetic material matrix, which are then drawn out of the test sample in one drawing experiment. Apart from the fact that such technology of preparation is difficult and is tied to a relatively high cost, the basic problem consists in that in the preparation of the test samples the adhesion of the fibres, i.e. the magnitude to be investigated, is influenced and changed in an uncontrolled manner, so that systematic errors of measurement result and the measurement is no longer representative. In carrying out drawing experiments of this kind, therefore, the following aims are considered to be priorities within the framework of the present invention:

a) The test sample preparation or the manufacture of the test sample bodies should take place as simply and quickly as possible.

b) Test sample bodies manufactured under identical conditions must yield reproducible results of measurement.

c) In the test sample preparation, the chemical and physical characteristics of the fibre and of the synthetic material matrix responsible for the adhesion forces should be controlledly variable.

SUMMARY OF THE INVENTION

Starting out from these aims, the object at the basis of the invention is therefore to improve the informational power of the drawing experiment in respect of the optimization of the mechanical characteristics of such composite material, under systematic, practically orientated investigations of the fibre adhesion in polymer composite materials.

This problem is solved according to the invention, in that a test sample of an individual fibre embedded in a synthetic material matrix is manufactured by melting a quantity of synthetic material in granular or powder form on a object holder, lowering the individual fibre in an axial direction perpendicular to the object holder and dipping it into the molten mass, and subsequently cooling the molten mass with the fibre embedded therein below melting point. The object holder together with the test sample adhering to it is then introduced into a force-distance measuring device, and the free end of the fibre is fixed at a fibre chucking device moveable in the direction of the fibre, whose travel is registered by a displacement transducer, and converted into a corresponding electrical signal. Subsequently, the drawing experiment is carried out and the associated force-distance diagram is drawn up.

After the drawing experiment, the synthetic material matrix is advantageously cut through at the height of the fibre embedding, perpendicular to the fibre axis, so that the sectional upper surface contains the hole corresponding to the fibre. The fibre diameter can then be determined by microscopic measurement of the hole.

In the manufacture of the test sample, the dipping process usefully takes place over a predetermined adjustable length, so that the embedding length of the fibre in the synthetic material matrix may be varied.

Further processing of the measurement signal may be simplified if in the force-measurement part, a force transducer is used whose path difference under varying force remains negligably small.

Accordingly to a further development of the invention, the embedding length of the fibre is determined during the drawing experiment from the difference of the displacement transducer positions during removal of the fibre from the synthetic matrix and after drawing out of the fibre and reversal of the direction of movement during striking of the fibre end against the matrix surface. This process allows a very exact determination of the embedding length.

A further development of the process according to the invention consists in that a sound emission analysis, in which the acoustic signals arising during the drawing experiment are registered and evaluated, is carried out simultaneously with the drawing experiment.

The device for carrying out the process according to the invention is based on a force-distance measuring device with a fixing device for the test sample and a fibre chucking device moveable in the direction of the fibre. The device is characterised according to the invention in that an electronic force transducer is mechanically connected with the fixing device for the test sample consisting of the synthetic matrix and the fibre embedded therein, for the measurement of force, that for the distance measurement an electronic displacement transducer is in connection with the fibre chucking device and the electrical signals yielded by the force or separation transducer are conveyed to the two channels of an XY recorder.

The force transducer consists preferably of electronic scales working according to the principle of the null method. This means that no path differences occur at the force transducer; i.e. a path-free force measurement is possible.

Further, the fibre chucking device is advantageously provided with clamping jaws for fixing the fibre end, of which at least one consists of a thermoplastic semi-rigid material. A problem-free, reliable fixing of the fibre end in the drawing experiment is thereby facilitated.

The adaptation of the force and distance signals necessary for the measurement value output usefully takes place in a computer, in which the parameter boundary conditions characteristic for the measurement may be simultaneously stored.

The following advantages are obtained with the invention:

The amount of work required for carrying out a drawing experiment including the associated manufacture of the test sample body (test sample preparation) remains within reasonable limits. The preconditions for the systematic investigation of a multiplicity of test samples with a manageable expenditure of labour are brought about.

Test sample bodies manufactured under identical conditions yield reproducible measurement results. According to experience, this is not always guaranteed with the experimental methods customary until now.

The simple and surveyable preparation technology in the manufacture of the test sample bodies allows both physical and chemical characteristics, both of the polymer matrix and of the fibre, to be systematically varied. Thus e.g. the influence of a surface preparation of the fibre, e.g. a simple treatment, the temperature control during embedding of the fibre, and the influence of the surface roughness of the fibre, may be taken into account.

The measurement of falsifying deformation effects during chucking of the fibre may be avoided.

The simultaneous investigation of the acoustic emission arising during a drawing experiment yields an important addition to the understanding of the microdeformation and relaxation effects unfolding at the boundary layer between fibre and synthetic material matrix.

The process according to the invention is also advantageously suited for investigating composite materials on the basis of thermally hardenable or cross-linkable polymers (duroplasts). In this case, for the preparation of the test sample body, the fibre is lowered and dipped not into a molten polymer mass but into a chemically cross linkable polymer mass.

In the following the invention is explained in greater detail with reference to drawings and examples of embodiment, where:

DETAILED DESCRIPTION OF THE INVENTION

Figure 1:
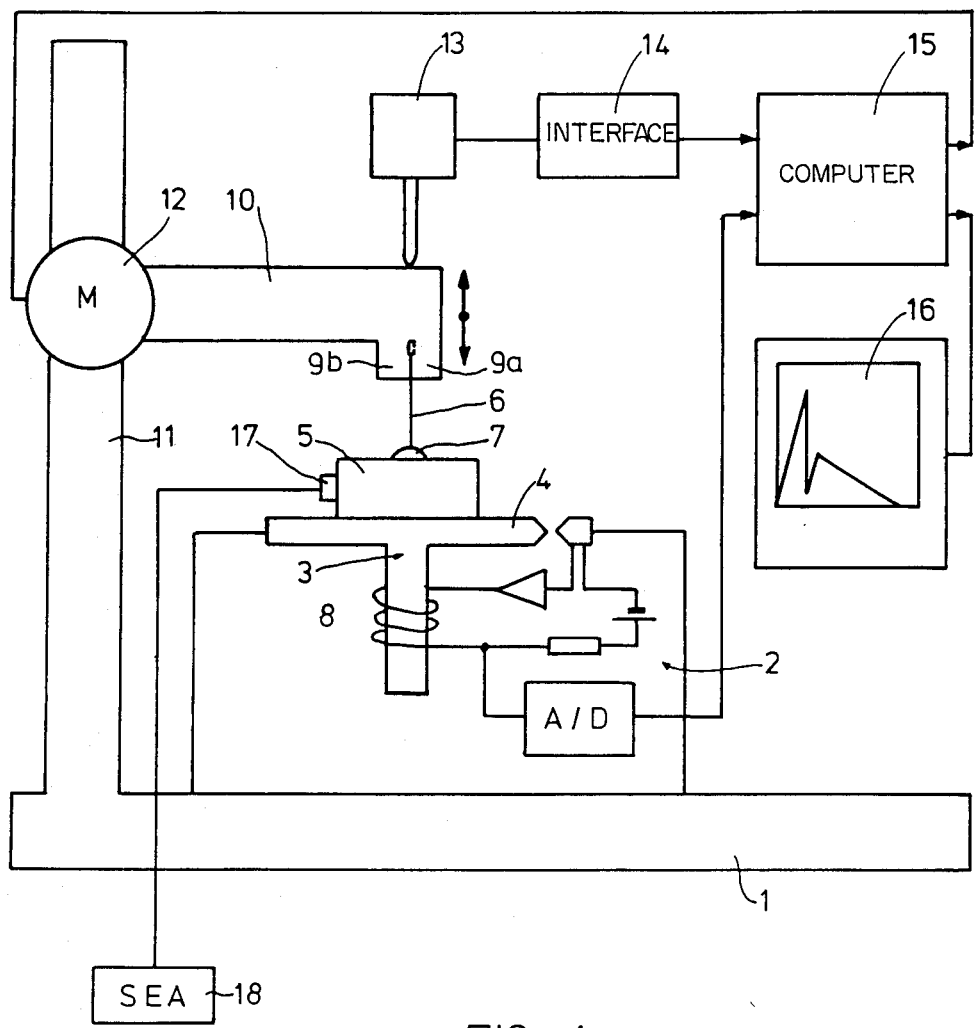
Figure 2:
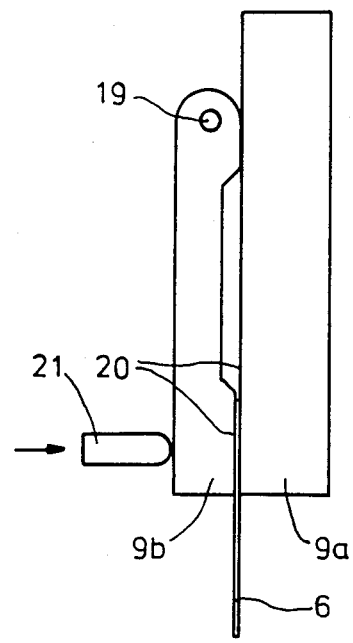
Figure 3:
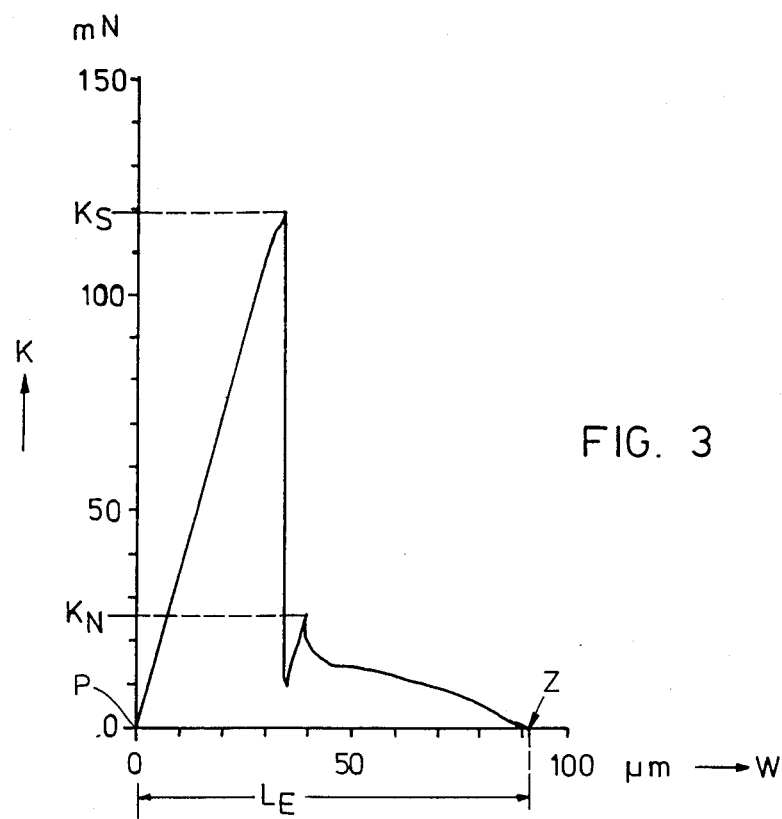

FIG. 1 shows the schematic construction of the measurement apparatus for the drawing experiment, FIG. 2 shows the chucking device for the fibre, FIG. 3 shows a typical force-distance measurement diagram picked up on the apparatus according to FIG. 1.

DETAILED DESCRIPTION OF THE INVENTION

In the measurement apparatus according to FIG. 1, a force transducer 2, which consists here of electronic scales 3, is mounted on a base plate 1. A test piece fixing device 5, which carries a test piece consisting of the fibre 6 and the polymer matrix 7, is attached to the scale pan 4 of said electronic scales 3. The electronic scales 3 function so that with a force loading (upward pull) through the electromagnet 8, an identically large opposing force is yielded (which brings the scale beam 4 back in to the balance position). The current flowing through the electromagnet 8 is then utilized as a measurement signal.

This kind of force measurement (null method) has the advantage that the force measurement is distancefree, i.e. that no displacement path is necessary for the force transducer, in order to yield a measurement signal. In place of electronic scales working according to the principle of the null method, a different force transducer (force sensor) customary in the trade could of course also be used, whose path difference in the regions of force measurement considered here is negligably small (<1 micrometer).

The upper end of the fibre 6 is firmly connected to the chucking device 10 by means of the gripping jaws 9a and 9b. The chucking device 10 may travel across a cogwheel mechanism (not shown) and a motor 12 arranged at the vertical carrier 11, in the direction of the fibre 6, i.e. perpendicular to the scale pan 4. If the chucking device 10 moves e.g. upwards, then a defined drawing force is exercised on the fibre 6, which may be measured with the force transducer 2. The distance travelled is registered by a distance transducer 13 which is in connection with the chucking device 10 and converted into a corresponding electrical signal. The force or distance measurement signals are optionally conveyed across an interface 14 to a computer 15 and printed out by printer 16 in the form of an x,y diagram. The y co-ordinate therein corresponds to the drawing force and the x co-ordinate to the distance travelled (cf also FIG. 3).

A sound sensor 17, which converts the sound signals resulting during the drawing out of the fibre 6 from the polymer matrix 7 into an electrical signal, is attached to the fixing device 5 of the test piece body 6, 7. These signals are then conveyed to a sound emission analyzer 18. Such devices are known in principle and described in the literature (see eg AG.Beattie, Acoustic Emission Principles and Instr.Journ. of Acoustic emission Vol 2, No. $\frac{1}{2}$ p. 95-128 (1983)). With the help of this device e.g. the frequency, the total energy, and the peak value of a sequence of acoustic signals may be determined. A determined acoustic signal sequence usually corresponds to a determined mechanical process, so that one speaks in this connection of a sound event. In the present case a sound emission analysis is carried out simultaneously with the drawing experiment, so that the sound signals resulting during the drawing out of the fibre 6 from the polymer matrix 7 may be analysed. It has been shown that the sound events occurring therein may be correlated with the mechanical processes taking place one after the other during drawing out of the fibre. For during the drawing out of the fibre, purely distinct sound events are observed, which may be assigned to the individual curve sections in the forcedistance diagram according to FIG. 3. The mechanical characteristics of a fibre composite material are definitively determined by the boundary layer between the fibre and the polymer matrix. One may assume that the sound emission analysis in connection with the drawing experiment delivers valuable clues to the boundary layer behaviour and thereby opens new paths to the optimization of such materials.

FIG. 2 shows the essential part of the fibre chucking device 10 with the clamping jaws 9a and 9b. The clamping jaw 9a consists of a polished metal plate, the clamping jaw 9b of a transparent synthetic material plate (e.g. PMMA), which is rotatable at its upper end about an axis 19. At its lower end the synthetic material plate 9b comprises a polished surface 20, as does the metal plate 9a. By means of an adjusting screw 21, a defined contact pressure may be exercised on the synthetic material plate 9b. The upper end of the fibre 6 is located between the two polished surfaces of the clamping jaws 9a and 9b and is thereby held and fixed in a defined manner. Additionally, the chucked part of the fibre 6 may be observed through the synthetic material plate and errors may be checked during chucking of the fibre.

The test sample body consisting of the fibre 6 and the polymer matrix 7 is manufactured in the following manner. A small quantity (e.g. 0.1 g) of the thermoplastic synthetic material to be investigated is applied in granular or powder form onto the specimen holder of the test piece fixing device 5 and heated to such a temperature that the synthetic material melts into a drop (as shown in FIG. 1) or into a film. In this drop or film, with the help of a device which is similarly constructed to the moveable chucking device 10 in FIG. 1, the fibre 6 to be investigated is lowered from above and dipped into the molten polymer mass. The length of dipping may therein be roughly pre-chosen via the stroke of the chucking device. Subsequently, the polymer mass is allowed to cool down again, below its melting point. The fibre is then embedded in the dipping region in the rigidified cap-shaped synthetic material matrix (FIG. 1). After melting and rerigidification of the polymer mass, the matrix 7 as a rule adheres fast to the surface of the specimen holder. An additional fitting may take place, if this would be required in individual cases.

The exact value of the embedding length may be determined with the help of the drawing experiment (see FIG. 3). In FIG. 3 the force-distance diagram of a drawing experiment is represented. The distance covered by the chucking device 10 is entered as the abscissa, and the drawing force measured with the force transducer 2 is entered as the ordinate. It will be seen that the force increases linearly with distance up to the value $K_S$. This region corresponds to an elastic reversible stretching of the fibre. Upon reaching the maximal force $K_S$, the fibre is released from the synthetic material matrix, so that the force drops to a very low value. Subsequently, a certain force $K_N$ must first be built up again, which is sufficient to overcome the adhesion friction of the fibre in the polymer matrix. The final region is characterised by a continuous decrease of force. This decrease is conditioned by the always diminishing residual length of the fibre in the polymer matrix. Finally, the force is zero, when the fibre is completely drawn out of the polymer matrix. This fact may be made use of as shown in FIG. 3 from the exact determination of the embedding length $L_E$. An alternative process for the determination of the embedding length $L_E$ consists in that the direction of movement of the chucking device is reversed after complete drawing out of the fibre, so that the fibre tip is lowered in the direction of the matrix 7 (FIG. 1). Upon striking of the fibre tip on the matrix 7 a small opposing force appears, which would appear in FIG. 3 as 'force-peak'. The position of this force-peak thus marks a point P, calculated from the zero point 2, the length $L_E$ of the region of the fibre embedded in the matrix material. The embedding length $L_E$ can thereby be obtained, in any case, with sufficient accuracy as the difference between the displacement transducer positions belonging to these two points. This process is to be preferred to the process for determining the embedding length described above because of its higher accuracy.

Besides the embedding length $L_E$, the diameter d of the fibre must also be obtained as a further geometric quantity. To this end the polymer matrix 7 is cut through perpendicular to the fibre at the height of the fibre embedding, after the drawing experiment, so that the surface of section contains the hole corresponding to the fibre. The fibre diameter may then be simply determined by microscopic measurement of the holes.

We claim:

1. In a process for determining the adhesion of an individual fibre embedded in a polymer matrix, including carrying out a drawing experiment wherein the fibre is drawn out of the polymer matrix and an associated force-distance diagram is simultaneously registered, the improvement wherein: a test sample of the individual fibre embedded in the polymer matrix is produced by melting a quantity of polymer mass in granular or powder form on an object holder, lowering the individual fibre in an axial direction perpendicular to the object holder dipping an end of the fibre into the molten polymer mass, and subsequently cooling the molten polymer mass below melting point; and the drawing experiment is carried out by introducing the object holder together with the test sample adhering to it into a force-distance measuring device, and fixing the free end of the fibre to a fibre chucking device moveable in the direction of the fibre, and converting a distance travelled by the fibre chucking device into an electrical signal with a displacement transducer.

2. The process according to claim 1, further comprising, after the drawing experiment, cutting through the polymer matrix at a height where the fibre is embedded, perpendicular to the fibre axis, such that the sectional upper surface contains the hole corresponding to the fibre, and determining the fibre diameter by microscopic measurement of the hole.

3. The process according to claim 1, wherein the step of dipping comprises dipping the into the molten mass over a predetermined adjustable length.

4. The process according to claim 1, further comprising performing a force-measurement with a force transducer whose path difference under varying force remains negligably small.

5. The process according to claim 1, further comprising determining the embedding length $L_E$ of the fibre in the polymer matrix from the difference of the displacement transducer position after removal of the fibre and the position after a reversal of the direction of movement and a striking of the fibre end against the surface of the polymer matrix.

6. The process according to claim 1, further comprising carrying out a sound emission analysis simultaneously with the drawing experiment.

* * * * *

UNITED STATES PATENT AND TRADEMARK OFFICE
CERTIFICATE OF CORRECTION

PATENT NO. : 4,856,342
DATED : Aug. 15, 1989
INVENTOR(S) : Bottenbruch et al.

It is certified that error appears in the above-identified patent and that said Letters Patent is hereby corrected as shown below:

Col. 3, lines 38 and 39    Delete "Detailed Description of the Invention" and substitute --Brief Description of the Drawings--

Col. 5, line 52    Delete "2" and substitute --Z--

Col. 6, line 41    Insert --fibre-- after "the"

Signed and Sealed this

Sixth Day of November, 1990

Attest:

HARRY F. MANBECK, JR.

*Attesting Officer*      *Commissioner of Patents and Trademarks*